US012334197B2

(12) United States Patent
Shaskey

(10) Patent No.: US 12,334,197 B2
(45) Date of Patent: Jun. 17, 2025

(54) APPLICATION TO CAPTURE A VIDEO AND EXTRACT INFORMATION FROM THE VIDEO

(71) Applicant: ShasKEYNOTE, LLC., Salt Lake City, UT (US)

(72) Inventor: David Shaskey, Salt Lake City, UT (US)

(73) Assignee: ShasKEYNOTE, LLC, Salt Lake City, UT (US)

( * ) Notice: Subject to any disclaimer, the term of this patent is extended or adjusted under 35 U.S.C. 154(b) by 252 days.

(21) Appl. No.: 18/306,924

(22) Filed: Apr. 25, 2023

(65) Prior Publication Data

US 2024/0161885 A1  May 16, 2024

Related U.S. Application Data

(63) Continuation-in-part of application No. 18/054,669, filed on Nov. 11, 2022.

(51) Int. Cl.
| | |
|---|---|
| *H04N 23/62* | (2023.01) |
| *G06F 21/62* | (2013.01) |
| *G06V 10/94* | (2022.01) |
| *G06V 20/40* | (2022.01) |
| *G16H 10/60* | (2018.01) |
| *H04N 5/765* | (2006.01) |

(52) U.S. Cl.
CPC ......... *G16H 10/60* (2018.01); *G06F 21/6245* (2013.01); *G06V 10/945* (2022.01); *G06V 20/47* (2022.01); *H04N 5/765* (2013.01); *H04N 23/62* (2023.01)

(58) Field of Classification Search
USPC ........................................... 348/243
See application file for complete search history.

(56) References Cited

U.S. PATENT DOCUMENTS

| | | | |
|---|---|---|---|
| 9,183,602 B2 | 11/2015 | O'Larte | |
| 10,320,903 B2 | 6/2019 | Newman et al. | |
| 2014/0095210 A1* | 4/2014 | Goss | G16H 10/60 705/3 |
| 2014/0222462 A1 | 8/2014 | Shakil et al. | |
| 2014/0278584 A1* | 9/2014 | Dart | G06Q 40/08 705/4 |

(Continued)

*Primary Examiner* — Nigar Chowdhury
(74) *Attorney, Agent, or Firm* — Maschoff Brennan

(57) ABSTRACT

A computing device may include processors configured to perform operations. The operations may include receiving a user input effective to indicate a client visit is to start. The operations may include instructing, based on the user input, a video camera to capture a visit video of the client visit. The operations may include receiving a user input effective to indicate a visit summary is to start. The operations may include instructing, based on the user input, the video camera to capture a summary video of the visit summary. The operations may include automatically saving the visit video and the summary video to a data storage location associated with the client. The operations may include authorizing a computing device to access the summary video saved to the data storage location to extract information from the summary video to a client record within a record application corresponding to the user.

20 Claims, 6 Drawing Sheets

(56) References Cited

U.S. PATENT DOCUMENTS

| | | | |
|---|---|---|---|
| 2014/0330579 A1* | 11/2014 | Cashman | G06Q 10/1095 |
| | | | 705/2 |
| 2014/0350961 A1* | 11/2014 | Csurka | G16H 10/60 |
| | | | 705/3 |
| 2015/0025912 A1* | 1/2015 | Kutty | G16H 15/00 |
| | | | 705/3 |
| 2015/0347686 A1 | 12/2015 | Ortiz et al. | |
| 2017/0230605 A1 | 8/2017 | Han et al. | |
| 2019/0272900 A1 | 9/2019 | Jancsary | |
| 2020/0043577 A1 | 2/2020 | Jiang et al. | |
| 2021/0335503 A1 | 10/2021 | Williams, III | |

* cited by examiner

APPLICATION TO CAPTURE A VIDEO AND EXTRACT INFORMATION FROM THE VIDEO

CROSS-REFERENCE TO RELATED APPLICATION

This patent application is a continuation-in-part of U.S. patent application Ser. No. 18/054,669 filed Nov. 11, 2022, titled "MEDICAL VIDEO CHARTING APPLICATION," which is incorporated in the present disclosure by reference in its entirety.

FIELD

The embodiments discussed in the present disclosure are related to an application to capture a video and extract information from the video.

BACKGROUND

Unless otherwise indicated in the present disclosure, the materials described in the present disclosure are not prior art to the claims in the present application and are not admitted to be prior art by inclusion in this section.

An individual that conducts visits with a client (e.g., a client visit, a client encounter, or a client interaction) in a professional capacity may maintain a client record that documents the client visit and describes relevant histories of the clients (e.g., the individual may perform client charting). For example, the client record may include lists and/or descriptions of topics discussed with the client, events that occurred to the client, results of previous actions, or any other appropriate information.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One or more embodiments of the present disclosure may include a computing device that includes one or more computer-readable storage media configured to store instructions. The computing device may also include one or more processors communicatively coupled to the one or more computer-readable storage media. The one or more processors may be configured to, in response to execution of the instructions, cause the computing device to perform operations. The operations may include receiving, via a graphical user interface (GUI), a first user input effective to indicate a client visit between a client and a user is to start. The operations may also include instructing, based on the first user input, a video camera to capture a visit video of the client visit. In addition, the operations may include receiving, via the GUI, a second user input effective to indicate a visit summary by the user is to start. Further, the operations may include receiving the visit video from the video camera. The operations may include instructing, based on the second user input, the video camera to capture a summary video of the visit summary. The operations may also include receiving the summary video from the video camera. In addition, the operations may include automatically saving the visit video and the summary video to a data storage location associated with the client. Further, the operations may include authorizing a remote computing device to access the summary video saved to the data storage location to extract information from the summary video corresponding to the visit summary to a client record within a record application corresponding to the user.

The object and advantages of the embodiments will be realized and achieved at least by the elements, features, and combinations particularly pointed out in the claims. Both the foregoing general description and the following detailed description are exemplary and explanatory and are not restrictive.

BRIEF DESCRIPTION OF THE DRAWINGS

Example embodiments will be described and explained with additional specificity and detail through the use of the accompanying drawings in which.

DETAILED DESCRIPTION

Figure 1:
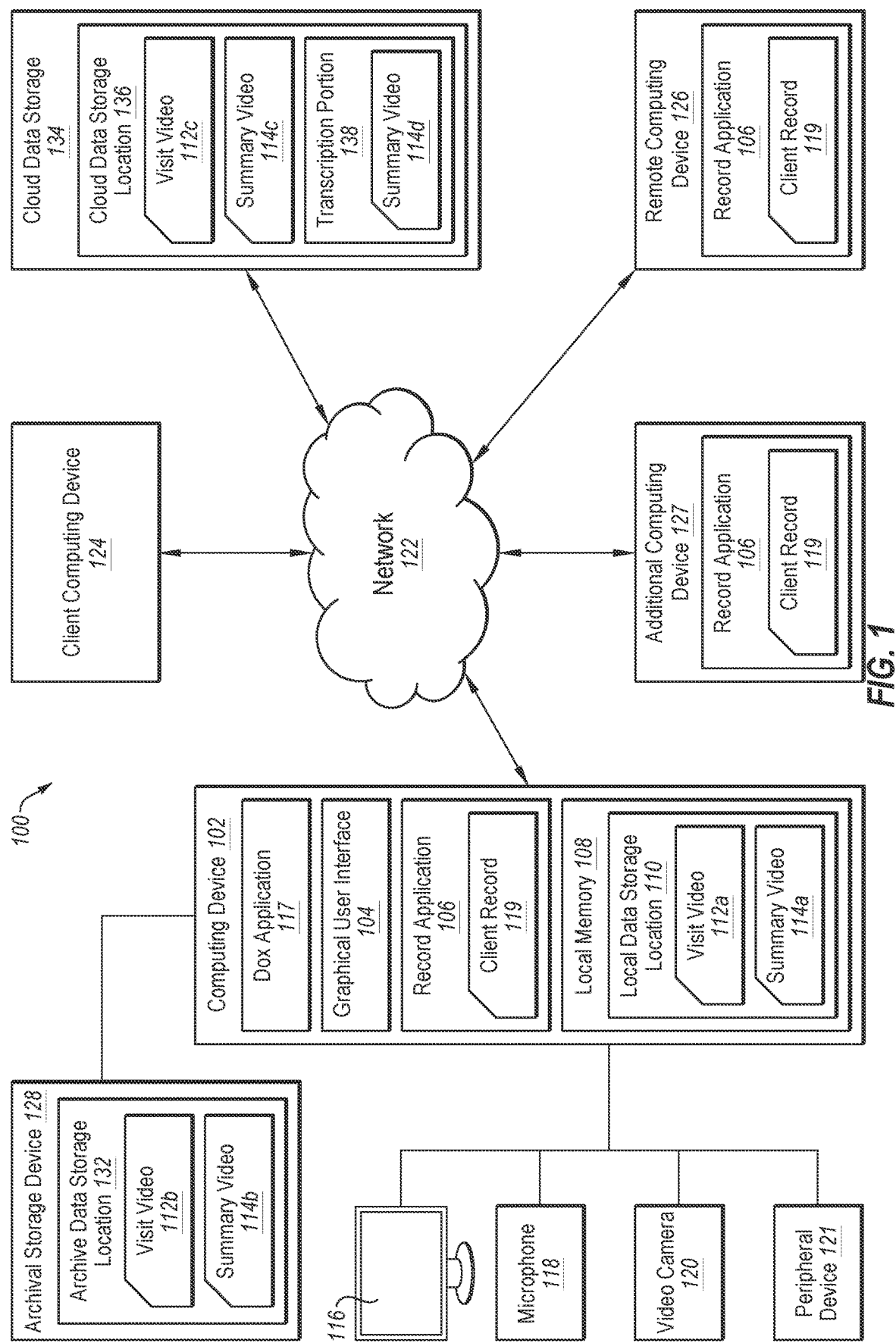
FIG. 1 illustrates a block diagram of an example system to extract information from the summary video and enter the information in the client record within the record application.

The client record may provide an overview of the relevant history of the client. For example, the client record may include medical records, medical histories, clinical data, demographics, vital signs, surgical histories, medications, treatment plans, allergies, laboratory results, radiological studies, immunization records, or some combination thereof of the client.

The user may review the client record to refresh their memory of important details corresponding to the client and to determine a course of action regarding the client (e.g., a treatment plan). The client record may be created, provided, and maintained electronically by a record application. In some embodiments, the client record may be created, provided, and maintained by a cloud-based record application, other remote record application, or a local record application. The client record including the relevant history of the client may improve care received by the client or improve a quality of service provided by the user.

In some professional fields, the user may spend one or more hours a working day entering information in client records. For example, surveys have found that all doctors spend an average of three hours per working day entering information in client records based on client visits that occurred that working day. Entering the information in client records and the amount of time used doing this is consistently the number one cause of professional burnout of users.

In addition, the amount of time used to enter information in client records takes time that the user could be using to provide service to clients.

Currently some users enter the information in client records during client visits, between client visits, at the end of a working day, or some combination thereof. This adds time to a workload of the users. In addition, entering the information in client records during client visits may reduce direct interaction between the users and clients, which may reduce a satisfaction level for the clients. Some users employ a scribe to enter the information in client records during client visits. However, the scribe dramatically increases a cost associated with providing services by the user and may be cost prohibitive. In addition, the scribe may not enter or may not be permitted to enter specific information directed to the client such as diagnoses and charges. Further, the scribe may not be familiar with the record application and may enter erroneous information in client records. Some users dictate the information and then hire a transcriptionist to enter the information in client records, which may also be cost prohibitive. The user or the scribe manually entering the information into the client records do not generate a summary that can be used for client education, litigation protection by the user, or both.

Some embodiments described in the present disclosure may include a computing device that includes a Dox application (e.g., a computer application). The Dox application may cause a video camera to capture a visit video of the client visit and a summary video of a summary of the client visit. In addition, the Dox application may authorize information to be extracted from the summary video and entered in a corresponding client record within the record application via a remote computing device.

The computing device may be communicatively coupled to a microphone, the video camera, a display, or some combination thereof. The display may be oriented such that the client can see a video stream of what is being recorded by the video camera. The video camera may record the visit video of the client visit and the summary video of the summary of the client visit. The microphone may capture audio for the visit video and the summary video. The Dox application may receive the visit video and the summary video from the video camera, the microphone, or both.

The Dox application may automatically save the visit video and the summary video to data storage locations (e.g., a local memory, a cloud data storage location, a folder, or some combination thereof) that are associated with the client. In particular, the Dox application may save the summary video to a transcription portion of the data storage locations. The Dox application may permit or otherwise authorize the remote computing device to access the summary video saved to the transcription portion to extract information from the summary video and to enter the extracted information in the client record within the record application.

In some embodiments, the Dox application may generate a resource locator link corresponding to the visit video, the summary video, or both. The Dox application may provide the resource locator link to the client to permit the client to access the visit video, the summary video, or both. In these and other embodiments, the resource locator link may permit the client to only access the visit video, the summary video, or both (e.g., read only access) or to access and download the visit video, the summary video, or both (e.g., read and write access). In some embodiments, the computing device may be communicatively coupled to an archival storage device. The Dox application may periodically archive the contents of the data storage locations to the archival storage device. For example, the user or an assistant of the user may provide user input via the GUI, the Dox application, or some combination thereof effective to cause the Dox application to archive the contents of the data storage locations to the archival storage device.

The Dox application may receive, via the GUI, a first user input effective to indicate the client visit between the client and the user is to start. In addition, the Dox application may instruct, based on the first user input, the video camera to capture the visit video of the client visit. Further, the Dox application may receive, via the GUI, a second user input effective to indicate the visit summary by the user is to start. The Dox application may instruct, based on the second user input, the video camera to capture the summary video of the visit summary.

The Dox application may receive the summary video, the visit video, or both from the video camera. In addition, the Dox application may automatically save the visit video and the summary video to the data storage location associated with the client. Further, the Dox application may authorize the remote computing device to access the summary video saved to the data storage location to extract information from the summary video corresponding to the visit summary to a client record within a record application corresponding to the user.

In some embodiments, aspects of the present invention are directed towards methods and equipment for medical video charting. Some embodiments of the present invention may comprise a kit comprising a laptop, a monitor, a web-enabled camera, a microphone, access to a cloud-based storage system, a hard drive storage for archiving, and a set of instructions for a method for medical video charting.

The Dox application may simplify the process to enter information in the client record in the record application. In addition, the Dox application may simplify the process for the user to interface with the computing device to obtain and save the visit video, the summary video, or both. Further, the Dox application may permit the user to be present and focus on the client during the client visit to improve the quality of service and care provided by the user. The Dox application may reduce the workload of the user, the cost associated with providing services by the user, or both.

In some embodiments, the summary video may be recorded with the client present to permit the client to listen and ensure accuracy of the details in the visit summary. The summary video may be recorded close in time to the client visit to reduce charting errors as opposed to performing visit summaries for multiple clients at the end of a working day. In some embodiments, the visit video, the summary video, or both that are archived may be used by the user to resolve conflicts with the client or during litigation.

The Dox application may improve the technological field of electronic record keeping by automatically saving duplicate copies of the summary video to reduce the likelihood of the summary video being erroneously deleted or lost due to technical issues. In addition, the Dox application may improve electronic record keeping by increasing accuracy of the client record due to the proximity in time that the visit summary occurs in relation to the client visit and by maintaining archived copies of the visit video and the summary video. Further, the Dox application may save the visit video, the summary video, or both to be used for client education, litigation protection by the user, or both.

The Dox application may improve entering information in the client record compared to entering the information using pen and paper or manual typing by using the summary video, which captures exactly what occurs and exactly what is said. In addition, the Dox application may improve entering information in the client record compared to entering the information using pen and paper by automatically saving copies of the visit video and the summary video and saving multiple versions of the summary video in multiple data storage locations. In contrast, medical records maintained using pen and paper are difficult to copy, archive, or store multiple copies of in different data storage locations. Each of these processes may add to the workload of the user rather than reducing it.

These and other embodiments of the present disclosure will be explained with reference to the accompanying figures. It is to be understood that the figures are diagrammatic and schematic representations of such example embodiments, and are not limiting, nor are they necessarily drawn to scale. In the figures, features with like numbers indicate like structure and function unless described otherwise.

FIG. 1 illustrates a block diagram of an example system 100 to extract information from a summary video 114a-d (generally referred to in the present disclosure as summary video 114) and enter the information in a client record 119 within a record application 106, in accordance with at least one embodiment described in the present disclosure. The system 100 may include a computing device 102, a network 122, a client computing device 124, a remote computing device 126, an additional computing device 127, an archival storage device 128, and a cloud data storage 134.

The computing device 102, the client computing device 124, the remote computing device 126, the additional computing device 127, or some combination thereof may include, by way of example and not limitation, personal computers (PCs), laptop computers, mobile devices, smartphones, tablet computers, personal digital assistants (PDAs), video players, handheld communication devices, embedded system controllers, consumer electronic devices, workstations, or any other suitable device. The computing device 102, the client computing device 124, the remote computing device 126, the additional computing device 127, or some combination thereof may be located at a single physical location (e.g., a single office space) or a different physical location (e.g., different office spaces).

The computing device 102 may include a Dox application 117. The Dox application 117 may include code and routines configured to enable the computing device 102 to perform one or more operations with respect to capturing visit video 112a-c (generally referred to in the present disclosure as visit video 112) and the summary video 114, saving the visit video 112 and the summary video 114, or authorizing the remote computing device 126 to access the summary video 114 to extract information from the summary video 114. Additionally or alternatively, the Dox application 117 may be implemented using hardware including a processor, a microprocessor (e.g., to perform or control performance of one or more operations), a field-programmable gate array (FPGA), or an application-specific integrated circuit (ASIC). In some other instances, the Dox application 117 may be implemented using a combination of hardware and software. In the present disclosure, operations described as being performed by the Dox application 117 may include operations that the Dox application 117 may direct the computing device 102, the cloud data storage 134, the archival storage device 128, or some combination thereof to perform.

The network 122 may include any communication network configured for communication of signals between any of the devices of the system 100. For example, the computing device 102, the client computing device 124, the remote computing device 126, the additional computing device 127, the cloud data storage 134, or some combination thereof may communicate via the network 122. The network 122 may be wired or wireless. The network 122 may have numerous configurations including a star configuration, a token ring configuration, or another suitable configuration. Furthermore, the network 122 may include a local area network (LAN), a wide area network (WAN) (e.g., the Internet), and/or other interconnected data paths across which multiple devices may communicate. In some embodiments, the network 122 may include a peer-to-peer network. The network 122 may also be coupled to or include portions of a telecommunications network that may enable communication of data in a variety of different communication protocols.

In some embodiments, the network 122 includes or is configured to include a BLUETOOTH® communication network, a Z-Wave® communication network, an Insteon® communication network, an EnOcean® communication network, a wireless fidelity (Wi-Fi) communication network, a ZigBee communication network, a HomePlug communication network, a Power-line Communication (PLC) communication network, a message queue telemetry transport (MQTT) communication network, a MQTT-sensor (MQTT-S) communication network, a constrained application protocol (CoAP) communication network, a representative state transfer application protocol interface (REST API) communication network, an extensible messaging and presence protocol (XMPP) communication network, a cellular communications network, any similar communication networks, a ZigBee automation, any similar automation network, or some combination thereof for sending and receiving data. The data communicated in the network 122 may include data communicated via short messaging service (SMS), multimedia messaging service (MMS), hypertext transfer protocol (HTTP), direct data connection, wireless application protocol (WAP), e-mail, smart energy profile (SEP), ECHONET Lite, OpenADR, or any other protocol that may be implemented with the computing device 102, the client computing device 124, the remote computing device 126, the additional computing device 127, or the cloud data storage 134.

The cloud data storage 134 may include any type of memory or data storage. In some embodiments, the cloud data storage 134 may include memory or data storage that is Health Insurance Portability and Accountability Act (HIPAA) compliant. The cloud data storage 134 may include web-based service software or applications, such as those provided by Microsoft OneDrive. The cloud data storage 134 may include network communication capabilities such that other devices in the system 100 may communicate with the cloud data storage 134. For example, the cloud data storage 134 may include a remote device that is accessed by the computing device 102, the client computing device 124, the remote computing device 126, the additional computing device 127, or some combination thereof via the network 122. In some embodiments, the cloud data storage 134 may include a computer-readable storage media for carrying or having computer-executable instructions or data structures stored thereon. The computer-readable storage media may include any available media that may be accessed by a general-purpose or special-purpose computer, such as a processor. For example, the cloud data storage 134 may include computer-readable storage media that may be tangible or non-transitory computer-readable storage media including RAM, ROM, EEPROM, CD-ROM, or other optical disk storage, magnetic disk storage or other magnetic storage devices, flash memory devices (e.g., solid state memory devices), or any other storage medium which may be used to carry or store desired program code in the form of computer-executable instructions or data structures and that may be accessed by a general-purpose or special-purpose computer. Combinations of the above may be included in the cloud data storage 134.

The computing device 102 may include a local memory 108. In some embodiments, the local memory 108 may include memory or data storage that is HIPAA compliant. The local memory 108 may include volatile memory such as RAM, persistent or non-volatile storage such as ROM, EEPROM, CD-ROM, or other optical disk storage, magnetic disk storage or other magnetic storage device, Not-And (NAND) flash memory or other solid state storage device, or other persistent or non-volatile computer storage medium. The local memory 108 may store computer instructions that may be executed by a processor (not illustrated in FIG. 1) to perform or control performance of one or more operations described in the present disclosure with respect to the Dox application 117.

The archival storage device 128 may include an external hard drive that includes volatile memory such as RAM, persistent or non-volatile storage such as ROM, EEPROM, CD-ROM, or other optical disk storage, magnetic disk storage or other magnetic storage device, Not-And (NAND) flash memory or other solid state storage device, or other persistent or non-volatile computer storage medium. The archival storage device 128 may store computer instructions that may be executed by a processor (not illustrated in FIG. 1) to perform or control performance of one or more operations described in the present disclosure with respect to the archival storage device 128. In some embodiments, the archival storage device 128 may include memory or data storage that is HIPAA compliant.

The computing device 102 may be communicatively coupled to a display 116, a peripheral device 121, or some combination thereof. The display 116 may be configured as one or more displays, like a liquid crystal display (LCD), light emitting diode (LED), or other type of display. The display 116 may be configured to present video, text captions, GUIs, and other data as directed by the computing device 102. The peripheral device 121 may include any device to allow the user to interface with the computing device 102. For example, the peripheral device 121 may include a mouse, a track pad, a keyboard, buttons, a camera, and/or a touchscreen, among other devices. The peripheral device 121 may receive input from the user and provide the input to the computing device 102. In some embodiments, the peripheral device 121 and the display 116 may be combined.

The computing device 102 may be communicatively coupled to a microphone 118 and a video camera 120. The microphone 118 may generally be used to record sound. For example, the microphone 118 may be used to record the sound of a conversation between the user and the client during the client visit or the sound of the user and the client during the visit summary. While labelled and described as a microphone, more generally the microphone 118 may include any type of sensor configured to capture sound and generate data representative of the captured sound. The video camera 120 may include a video camera or other device capable of generating a video of a scene. While labelled and described as a video camera, more generally the video camera 120 may include any type of sensor configured to capture video of the scene and generate data representa-tive of the captured video. While illustrated as separate components, the microphone 118 and the video camera 120 may be combined into a single component.

The archival storage device 128 may be communicatively coupled to the computing device 102. The archival storage device 128 may include any type of memory or data storage that is external to the computing device 102. For example, the archival storage device 128 may include a computer-readable storage media for storing data structures thereon. The archival storage device 128 may include any available media that may be accessed by the computing device 102. For example, the archival storage device 128 may include computer-readable storage media that may be tangible or non-transitory computer-readable storage media including RAM, ROM, EEPROM, CD-ROM, or other optical disk storage, magnetic disk storage or other magnetic storage devices, flash memory devices (e.g., solid state memory devices), or any other storage medium which may be used to carry or store desired data structures and that may be accessed by the computing device 102.

The record application 106 may be accessed via the computing device 102, the additional computing device 127, the remote computing device 126, or some combination thereof. The record application 106 may be a repository for client records (e.g., the client record 119), notes and/or information regarding client visits with the user, or any other appropriate information. The client record 119 may be created, provided, and maintained electronically by the record application 106. For example, notes regarding a plan of action corresponding to the client within the client record 119 may be accessed and updated via the record application 106. As another example, a medical history of the client within the client record 119 may be accessed and updated via the record application 106. In some embodiments, the record application 106 may include an electronic medical record (EMR). In these and other embodiments, the record application 106 may include a cloud-based record application or other remote record application.

In some embodiments, a local data storage location 110 of the local memory 108, a cloud data storage location 136 of the cloud data storage 134, or both may be associated with the client. In these and other embodiments, the local data storage location 110, the cloud data storage location 136, or both may be folders representative of a portion of memory of the local memory 108 or the cloud data storage 134. For example, the local data storage location 110 may be a folder representative of a portion of the local memory 108 and the cloud data storage location 136 may be a folder representative of a portion of the cloud data storage 134.

In some embodiments, the local data storage location 110, the cloud data storage location 136, or both may include one or more sub-data storage locations (e.g., sub-folders). For example, the computing device 102 may create a sub-data storage location (e.g., a transcription portion) (not illustrated in FIG. 1) of the local data storage location 110 and the cloud data storage 134 may create a sub-data storage location (e.g., a transcription portion 138) of the cloud data storage location 136.

The local memory 108 is illustrated as including one local data storage location 110 for simplicity. More generally, the local memory 108 may include any appropriate number of instances of local data storage locations (e.g., folders). For example, the local memory 108 may include two, three, four, five, or more instances (e.g., folders) of the local data storage locations 110. In some embodiments, each instance of the local data storage location 110 may correspond to a different client of the user. In other embodiments, each instance of the local data storage location 110 may correspond to a different period of time. For example, each instance of the local data storage location 110 may correspond to a different day, a different week, a different month, or a different year.

The cloud data storage 134 is illustrated as including one cloud data storage location 136 for simplicity. More generally, the cloud data storage 134 may include any appropriate number of instances of cloud data storage locations (e.g., folders). For example, the cloud data storage 134 may include two, three, four, five, or more instances (e.g., folders) of the cloud data storage location 136. In some embodiments, each instance of the cloud data storage location 136 may correspond to a different client of the user. In other embodiments, each instance of the cloud data storage location 136 may correspond to a different period of time. For example, each instance of the cloud data storage location 136 may correspond to a different day, a different week, a different month, or a different year.

The Dox application 117 may cause the computing device 102, the cloud data storage 134, or both to organize or otherwise arrange the different instances of the local data storage location 110 or the different instances of the cloud data storage location 136 based on corresponding information. For example, the different instances of the local data storage location 110 or the different instances of the cloud data storage location 136 may be organized or arranged chronologically based on a date/time of last access, chronologically based on a date/time of last write, chronologically based on a date/time of creation, or alphabetically based on a title or a label.

The number of instances of the cloud data storage location 136 and/or the number of sub-data storage locations may correspond to the number of instances of the local data storage location 110 and/or the number of sub-data storage locations or vice versa. For example, if the local memory 108 includes forty-five instances of the local data storage location 110 (e.g., forty-five folders), the cloud data storage 134 may include forty-five instances of the cloud data storage location 136. As another example, if the local data storage location 110 includes three sub-data storage locations (e.g., sub-folders), the cloud data storage location 136 may include three sub-data storage locations (e.g., sub-folders).

The computing device 102 may include a GUI 104 that is presented to the user via the display 116 or another display. The GUI 104 may be presented as a web browser or an application that is native to the computing device 102. The GUI 104 may guide the user through the process of generating and storing the visit video 112 and/or the summary video 114, extracting information from the summary video 114 to the client record 119 within the record application 106, or some combination thereof. For example, one or more elements of the GUI 104 may be presented to the user via which the user may provide user input effective to perform operations described in the present disclosure. The Dox application 117, the GUI 104, or both may be installed on the computing device 102. Prior to operation, the Dox application 117 may authorize or authenticate the computing device 102 as a computing device permitted to run the Dox application 117, the GUI 104, or both.

In some embodiments, the Dox application 117 may receive user input (e.g., via the peripheral device 121 selecting a field within the GUI 104) effective to identify the client via the GUI 104. For example, the user input may indicate a name of the client, a client identification number, a matter docket number, or any other appropriate identifying information of the client. The Dox application 117 may change the label or the title of the local data storage location 110 based on the identity of the client. For example, if the user input indicates that the name of the client is "John Smith," the Dox application 117 may change the label or the title of the local data storage location 110 to "John Smith." In addition, the Dox application 117 may instruct the cloud data storage 134 to change the label or the title of the cloud data storage location 136 based on the identity of the client.

The Dox application 117 may receive user input (e.g., via the peripheral device 121 selecting a field within the GUI 104) effective to indicate that the client visit is to start. The Dox application 117 may instruct and/or cause the video camera 120 to capture the visit video of the client visit. During the client visit, the user may ask the client to authorize video recording of the client visit and a response by the client is provided and recorded. In addition, during the client visit, the user and the client may discuss items that are related to a purpose of the client visit. For example, the user and the client may discuss items that are of concern to the client and/or the user, events that occurred to the client, results of previous actions taken by the client and/or the user, or any other appropriate items related to the purpose of the client visit. As another example, the client visit may include a doctor visit in which the client is a patient, and the user is a doctor that conducts a medical exam of the patient for medical concerns or other medical items.

After the client visit has ended, the Dox application 117 may receive the visit video 112 from the microphone 118, the video camera 120, or both. For example, the Dox application 117 may receive the visit video 112 representative of audio captured by the microphone 118, visuals within the scene captured by the video camera 120, or both during the client visit. The Dox application 117 may determine that the client visit has ended and that the visit video 112 is to be received based on user input provided via the GUI 104.

After the client visit has ended, the Dox application 117 may receive user input (e.g., via the peripheral device 121 selecting a field within the GUI 104) effective to indicate that the visit summary is to start. In some embodiments, this user input may also be effective to indicate that the client visit has ended. The Dox application 117, based on the user input, may instruct and/or cause the video camera 120 to capture the summary video 114 of the visit summary. During the visit summary, the user may summarize the client visit, report on items that were discussed during the client visit, describe plans of action, indicate billing matters such as billing codes, state professional determinations, or record any other appropriate information. In some embodiments, the Dox application 117 may receive via the GUI 104 user input effective to indicate the visit summary has ended.

The Dox application 117 may receive the summary video 114 from the microphone 118, the video camera 120, or both. For example, the Dox application 117 may receive the summary video 114 representative of audio captured by the microphone 118, visuals within the scene captured by the video camera 120 during the visit summary, or both.

The Dox application 117 may automatically save the visit video 112, the summary video 114, or both to data storage locations associated with the client. In some embodiments, the Dox application 117 may automatically save the visit video 112 in response to the user input effective to indicate that the visit summary is to start. In other embodiments, the Dox application 117 may automatically save the visit video 112 and the summary video 114 in response to the user input effective to indicate the visit summary has ended.

In some embodiments, the Dox application 117 may automatically save a copy of the visit video 112a, a copy of the summary video 114a, or both to the local data storage location 110. In these and other embodiments, the Dox application 117 may automatically cause a copy of the visit video 112c, a copy of the summary video 114c, another copy of the summary video 114d, or some combination thereof to be saved to the cloud data storage location 136. Additionally or alternatively, the Dox application 117 may cause the copy of the summary video 114d to be saved to the transcription portion 138 of the cloud data storage location 136, the copy of the summary video 114c to a different portion of the cloud data storage location 136, or both.

In some embodiments, the Dox application 117 may save the copy of the visit video 112a and the copy of the summary video 114a to the local data storage location 110 in sync with causing the copy of the visit video 112c and the copies of the summary video 114c-d to be saved to the cloud data storage location 136. In these and other embodiments, the Dox application 117 may automatically create the sub-data storage locations (e.g., sub-folders) or automatically cause the cloud data storage 134 to create the sub-data storage locations (e.g., sub-folders) based on receiving the summary video 114.

The Dox application 117 may authorize the remote computing device 126 to access the summary video 114 saved to the data storage locations. In addition, the Dox application 117 may authorize information to be extracted from the summary video 114 and entered in the client record 119 within the record application 106 by the remote computing device 126. In some embodiments, the Dox application 117 may authorize the remote computing device 126 to access only the copies of the summary video 114c-d saved to the cloud data storage location 136. In these and other embodiments, the Dox application 117 may authorize the remote computing device 126 to access only the copy of the summary video 114d saved to the transcription portion 138.

The remote computing device 126 may open and display the summary video 114 to extract information from the summary video 114. In some embodiments, a user of the remote computing device 126 may manually transcribe the audio or information included in the summary video 114 into written form in the client record 119. In other embodiments, an artificial intelligence (AI) program may transcribe the audio or information included in the summary video 114 into written form in the client record 119. The extracted information may be entered into the client record 119 via the record application 106 on the remote computing device 126. For example, the user of the remote computing device 126 or the AI program may complete all charting tasks corresponding to the summary video 114 in the client record 119.

In some embodiments, the Dox application 117 may authorize the remote computing device 126 to only have read access to the summary video 114. For example, the remote computing device 126 may only be authorized to display the summary video 114. In other embodiments, the Dox application 117 may authorize the remote computing device 126 to have read and write access to the summary video 114. For example, the remote computing device 126 may be authorized to display and then delete the summary video 114. As another example, the remote computing device 126 may be authorized to display and then delete only the copy of the summary video 114d saved to the transcription portion 138. In some embodiments, the Dox application 117 may authorize the remote computing device 126 to only have read access to the summary video 114 until the user or the AI program sign the client record 119.

After the audio or information included in the summary video 114 is entered into the client record 119, the user may access the client record 119 via any computing device with access to the record application 106. For example, the user may access the client record 119 via the computing device 102, the additional computing device 127, or both.

The computing device 102 may be communicatively coupled to the archival storage device 128. The archival storage device 128 may include an archive data storage location 132. The Dox application 117 may periodically archive the contents of the local data storage location 110 to the archival storage device 128. For example, the Dox application 117 may archive the contents of the local data storage location 110 to the archival storage device 128 weekly, monthly, quarterly, yearly, or any other periodic amount of time.

In some embodiments, during the archiving, the Dox application 117 may create or cause the archival storage device 128 to create an archive data storage location 132 that corresponds to the local data storage location 110, the cloud data storage location 136, or both. In these and other embodiments, the Dox application 117 may save or cause the archival storage device 128 to save a copy of the visit video 112b, a copy of the summary video 114b, or both to the archive data storage location 132. Additionally or alternatively, the Dox application 117 may save or cause the archival storage device 128 to save duplicate copies of the visit video 112, the summary video 114, or both. In some embodiments, the Dox application 117 may save or cause the archival storage device 128 to save the copy of the visit video 112c, the copy of the summary video 114c, or both to the archive data storage location 132. In these and other embodiments, the Dox application 117 may save or cause two or more copies of the visit video 112, the summary video 114, or both to be saved to the archive data storage location 132. In some embodiments, the copy of the visit video 112c, the copy of the summary video 114c, or both saved to the archival storage device 128 may be used for litigation protection by the user if the client claims malpractice or other inappropriate actions were made by the user during the client visit, client treatments, or any other action taken with regard to the client.

In some embodiments, the Dox application 117 may cause the label or the title of the archive data storage location 132 to correspond to the label or title of the local data storage location 110. For example, if the label or the title of the local data storage location 110 is "John Smith," the Dox application 117 may instruct the archival storage device 128 to name the archive data storage location 132 "John Smith" as well.

The Dox application 117 may delete the contents of the local data storage location 110 after performing the archiving. The Dox application 117 may delete the copy of the visit video 112a, the copy of the summary video 114a, or both after performing the archiving. Additionally or alternatively, the Dox application 117 may delete or cause the cloud data storage 134 to delete the copy of the visit video 112c, the copy of the summary video 114c, the copy of the summary video 114d, or some combination thereof after performing the archiving.

The Dox application 117 may generate a resource locator link that directs computing devices to the visit video 112. The resource locator link may direct computing devices to the copy of the visit video 112c saved to the cloud data storage location 136. The Dox application 117 may provide the resource locator link to the client computing device 124 to permit the client to access or view the visit video 112. For example, the Dox application 117 may provide the resource locator link to the client computing device 124 embedded in an email.

Following the resource locator link may authorize the client computing device 124 to access the visit video 112, view the visit video 112, download the visit video 112, access the summary video 114, view the summary video 114, download the summary video 114, or some combination thereof. The resource locator link may include an expiration date or time after which the resource locator link expires and no longer permits the client computing device 124 to access or view the visit video 112. Additionally or alternatively, the Dox application 117 may determine whether the client computing device 124 downloads the visit video 112. In response to the client computing device 124 downloading the visit video 112, the Dox application 117 may cause the resource locator link to become invalid and prevent future access to the visit video 112.

In some embodiments, the display 116 may be oriented such that the client can see a video stream of what is being recorded by the video camera 120 during the client visit, the visit summary, or both.

Modifications, additions, or omissions may be made to the system 100 without departing from the scope of the present disclosure. For example, in some embodiments, the system 100 may include any number of other components that may not be explicitly illustrated or described. As another example, the system 100 may include two or more video cameras 120, two or more microphones 118, two or more displays 116, or some combination thereof. As yet another example, the additional computing device 127, the remote computing device 126, the client computing device 124, or some combination thereof may be omitted.

Figure 2A:
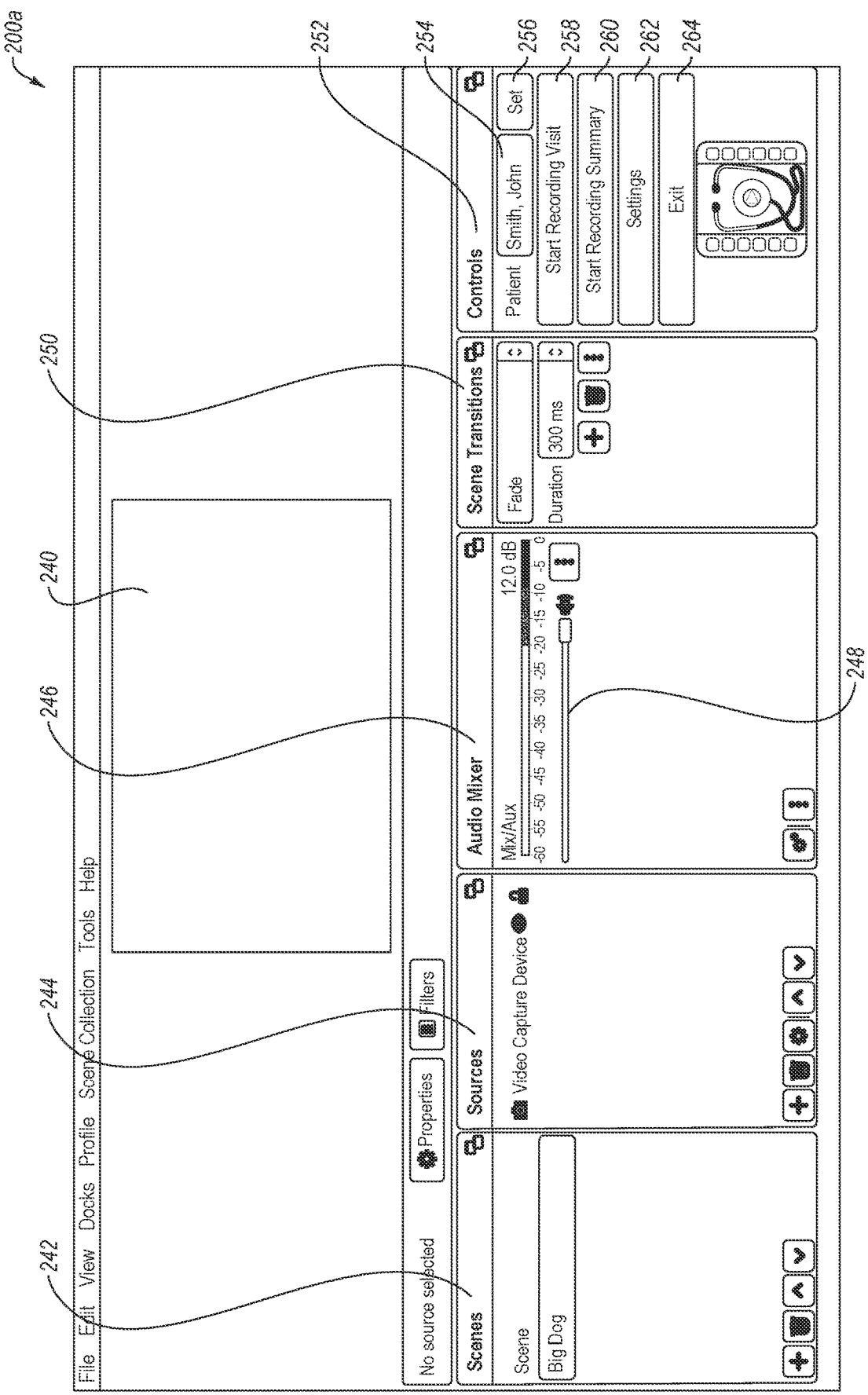
FIGS. 2A and 2B illustrate example GUIs that may be implemented in a computing device of FIG. 1.
Figure 2B:
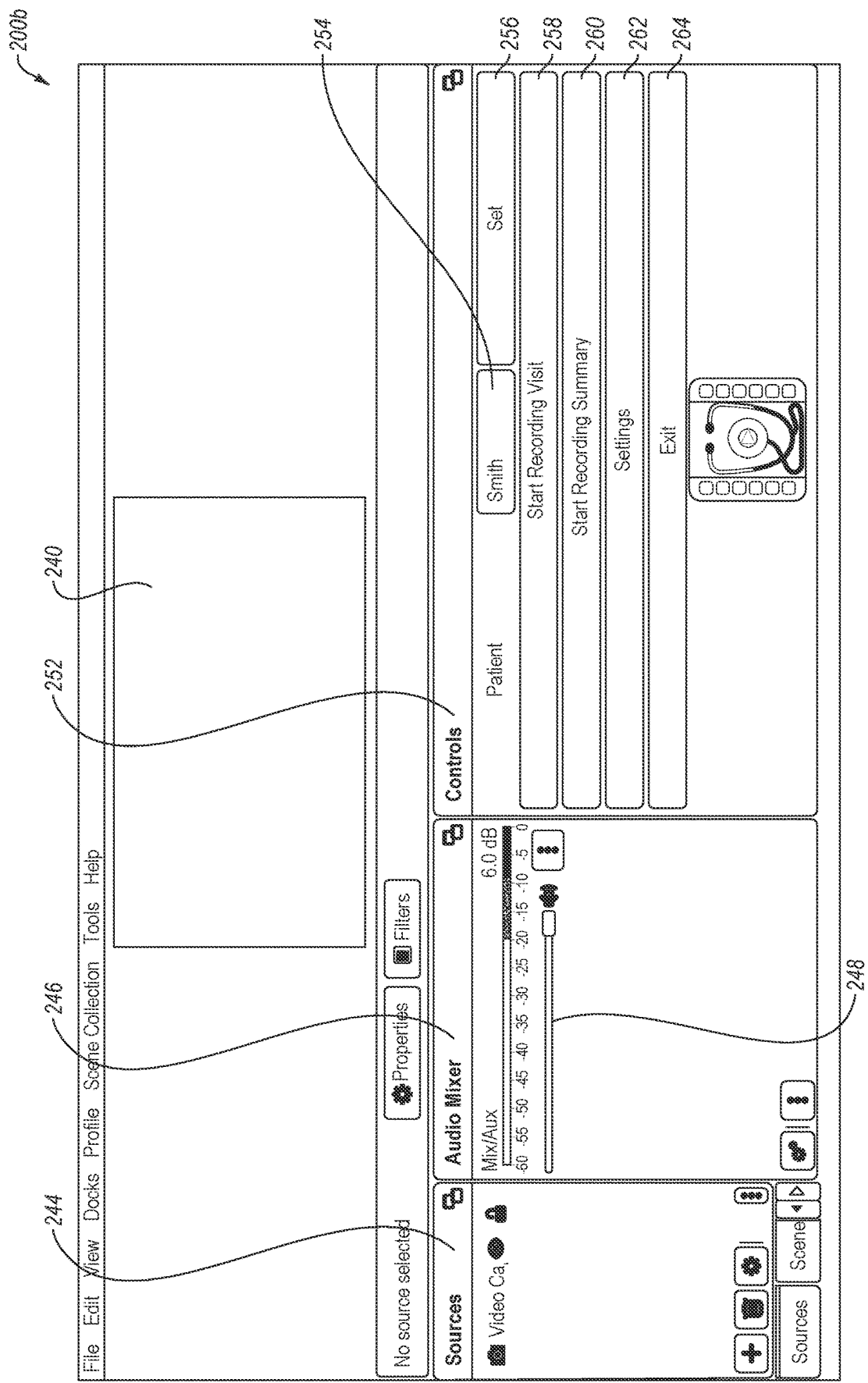

FIGS. 2A and 2B illustrate example GUIs 200a-b that may be implemented in the computing device 102 of FIG. 1, in accordance with at least one embodiment described in the present disclosure. In some embodiments, the GUIs 200a-b may be implemented as part of the Dox application 117. In these and other embodiments, the GUIs 200a-b may correspond to the GUI 104 of FIG. 1. The GUIs 200a-b may include a "Scenes" field 242, a "Sources" field 244, an "Audio Mixer" field 246, a display field 240, a "Scene Transitions" field 250, a "Controls" field 252, or some combination thereof.

The Scenes field 242 may be implemented to permit the user to provide user input effective to select a scene in which a video camera (e.g., the video camera 120 of FIG. 1), a microphone (e.g., the microphone of FIG. 1), or both capture audio and visuals within. The Sources field 244 may permit the user to provide user input effective to select a source of the visit video, the summary video, or both. The Audio Mixer field 246 may include a volume bar 248. The volume bar 248 may be implemented to permit the user to provide user input effective to adjust a level of a volume of the audio captured during the client visit or the visit summary. In addition, the Audio Mixer field 246 may be implemented to display a volume level (e.g., a decibel level) of the audio currently being captured. The Scene Transitions field 250 may be implemented to permit the user to provide user input effective to select a transition type between scenes of the visit video, the summary video, or both. The display field 240 may be populated with a video stream to display what is being captured by the video camera.

The Controls field 252 may include an identity field 254, a "Set" field 256, a "Start Recoding Visit" field 258, a "Start Recording Summary" field 260, a "Settings" field 262, an "Exit" field 264, or some combination thereof. The identify field 254 may be implemented to permit the user to provide user input effective to identify the client. For example, the identify field 254 may permit the user to type in the name of the client, the client identification number, the matter docket number, or any other appropriate identifying information of the client. The example shown in FIG. 2A includes the name "Smith, John" and the example shown in FIG. 2B includes the name "Smith." The Set field 256 may be implemented to permit the user to set the identity of the client and cause the corresponding data storage locations (e.g., the local data storage location 110, the cloud data storage location 136, or both to be named accordingly). For example, the user may select the Set field 256 by clicking on it to set the identity of the client.

The Start Recording Visit field 258 may be implemented to permit the user to provide user input effective to indicate that the client visit between the client and the user is to start. For example, the user may select the Start Recording Visit field 258 by clicking on it. The Start Recording Summary field 260 may be implemented to permit the user to provide user input effective to indicate that the visit summary by the user is to start. For example, the user may select the Start Recording Summary field 260 by clicking on it.

The Settings field 262 may be implemented to permit the user to provide user input effective to access settings of the GUIs 200a-b, the Dox application 117, or both. The Exit field 264 may be implemented to permit the user to provide user input effective to exit the GUIs 200a-b, the Dox application 117, or both.

Figure 3:
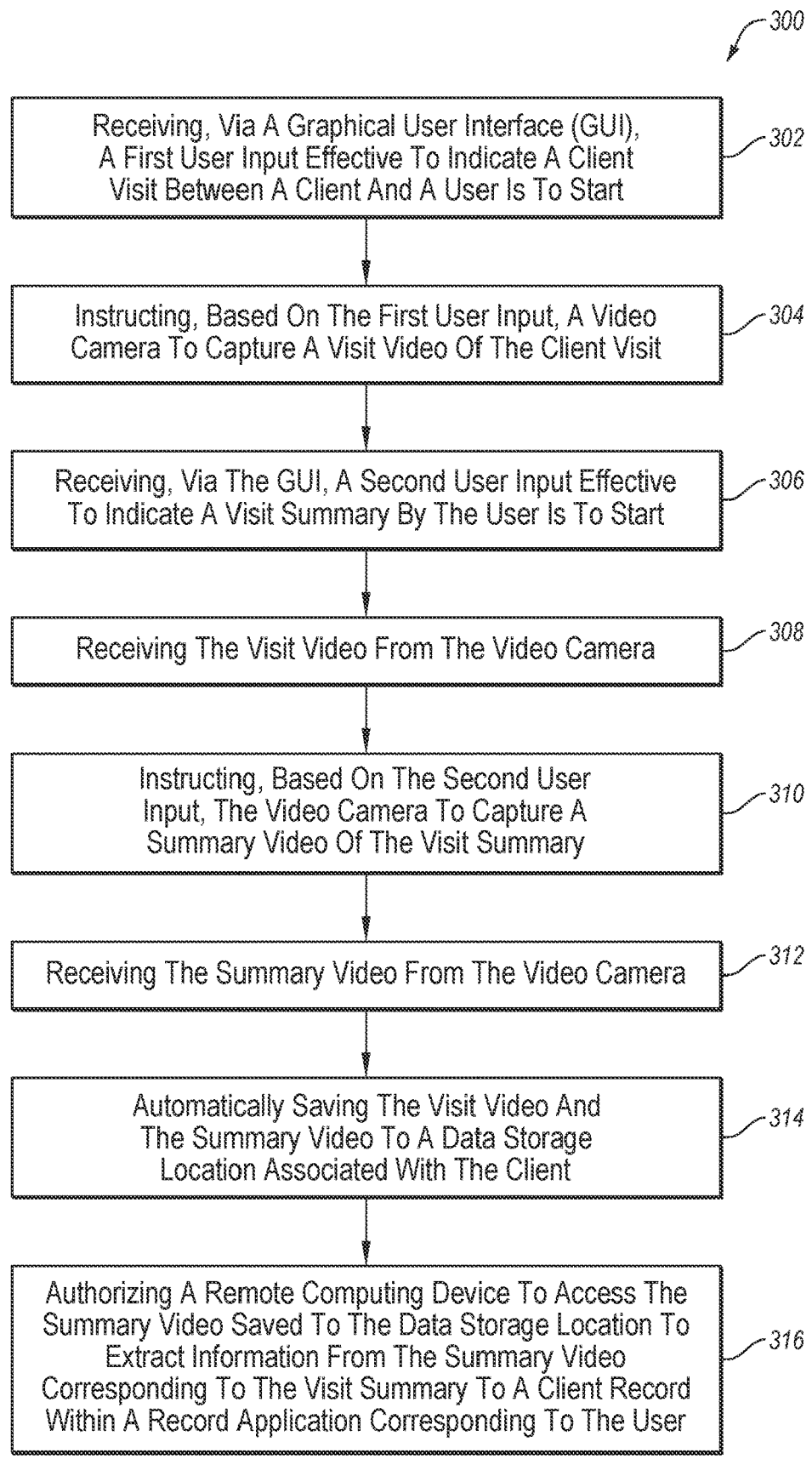
FIG. 3 illustrates a flowchart of an example method to extract information from the summary video to the client record within the record application.

FIG. 3 illustrates a flowchart of an example method 300 to extract information from the summary video 114 to the client record 119 within the record application 106, in accordance with at least one embodiment described in the present disclosure. The method 300 may be performed by any suitable system, apparatus, or device with respect to recording the summary video or the visit video and/or extracting information from the summary video 114 to the client record 119 within the record application 106. For example, the Dox application 117 102 may cause the computing device 102, the video camera 120, the microphone 118, the cloud data storage 134, the remote computing device 126, or some combination thereof of FIG. 1 to perform of one or more of the operations associated with the method 300. The method 300 may include one or more blocks 302, 304, 306, 308, 310, 312, 314, or 316. Although illustrated with discrete blocks, the steps and operations associated with one or more of the blocks of the method 300 may be divided into additional blocks, combined into fewer blocks, or eliminated, depending on the particular implementation.

At block 302, a first user input effective to indicate a client visit between a client and a user is to start may be received via a GUI. For example, the Dox application 117 of FIG. 1 may receive the user input by the user selecting a "Start Recording Visit" field within the GUI 104 via the peripheral device 121.

At block 304, a video camera may be instructed, based on the first user input, to capture a visit video of the client visit. For example, the video camera 120, the microphone 118, or both of FIG. 1 may record audio and/or visuals within a scene during the client visit as the visit video.

At block 306, a second user input effective to indicate a visit summary by the user is to start may be received via the GUI. For example, the Dox application 117 of FIG. 1 may receive the user input by the user selecting a "Start Recording Summary" field within the GUI 104 via the peripheral device 121.

At block 308, the visit video may be received from the video camera. For example, the video camera 120, the microphone 118, or both of FIG. 1 may provide the visit video to the computing device 102.

At block 310, the video camera may be instructed, based on the second user input, to capture a summary video of the visit summary. For example, the video camera 120, the microphone 118, or both of FIG. 1 may record audio and/or visuals within a scene during the visit summary as the summary video. At block 312, the summary video may be received from the video camera. For example, the video camera 120, the microphone 118, or both of FIG. 1 may provide the summary video to the computing device 102.

At block 314, the visit video and the summary video may be automatically saved to a data storage location associated with the client. For example, the Dox application 117 of FIG. 1 may automatically save or cause to be saved the visit video 112, the summary video 114, or both to the local data storage location 110, the cloud data storage location 136, or both upon receiving the visit video 112, the summary video 114, or both.

At block 316, a remote computing device may be authorized to access the summary video saved to the data storage location to extract information from the summary video corresponding to the visit summary to a client record within a record application corresponding to the user. For example, the Dox application 117 of FIG. 1 may authorize the remote computing device 126 to access the copy of the summary video 114d saved to the transcription portion 138 of the cloud data storage location 136 to extract information and enter it in the client record 119 within the record application 106.

Modifications, additions, or omissions may be made to the method 300 without departing from the scope of the present disclosure. For example, the operations of method 300 may be implemented in differing order. Additionally or alternatively, two or more operations may be performed at the same time. Furthermore, the outlined operations and actions are only provided as examples, and some of the operations and actions may be optional, combined into fewer operations and actions, or expanded into additional operations and actions without detracting from the essence of the described embodiments.

Figure 4:
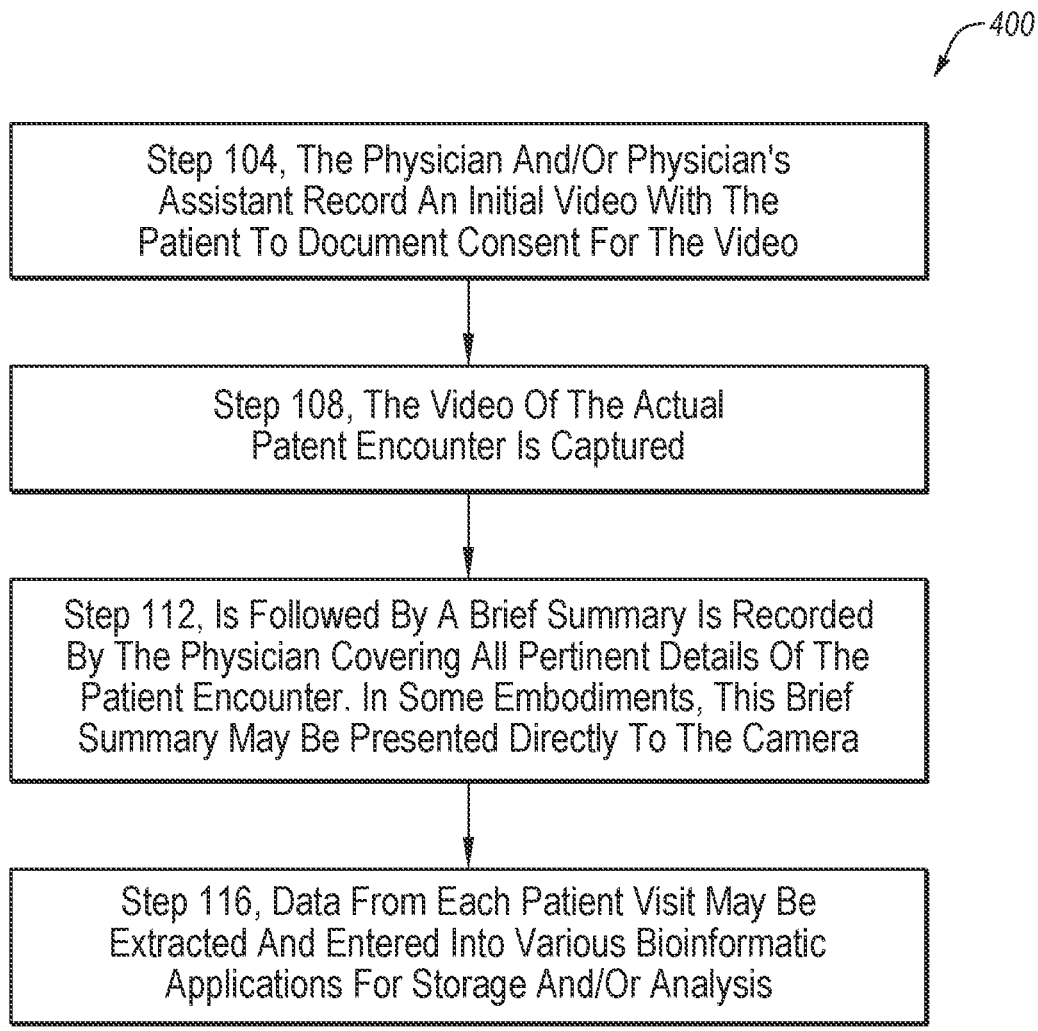
FIG. 4 provides a flowchart of an exemplary method is accordance with aspects of the present invention.

FIG. 4 provides a flowchart 400 of an exemplary method is accordance with aspects of the present invention. At step 104, the physician and/or physician's assistant record an initial video with the patient to document consent for the video. At step 108, the video of the actual patient encounter is captured. The term "patient encounter", as used herein is a broad term which may include but is not limited to, routine check-ups, urgent care appointments, in-patient rounds, telehealth consultations, and the like. The patient encounter may comprise but not be limited to review of patient medical history, physical examination, discussion and/or consultation with patient and/or the patient's family members regarding subjects including but not limited to diagnosis, evaluation, treatment, and follow-up recommendations and the like. At step 112, is followed by a brief summary is recorded by the physician covering all pertinent details of the patient encounter. In some embodiments, this brief summary may be presented directly to the camera. This represents a complete patient encounter and requires no additional record keeping or charting on the part of the physician to document the visit.

After the patient encounter, at step 116, data from each patient visit may be extracted and entered into various bioinformatic applications for storage and/or analysis. In some embodiments, data may be extracted from the video record of the patient encounter via an AI enabled transcription application. In other embodiments, data may be extracted manually by the physician's assistant and/or by the physician. In some embodiments, transcriptions may be delayed for a later time for more efficient time use. At step 120, the video of the complete patient encounter may be archived for later review if necessary.

Figure 5:
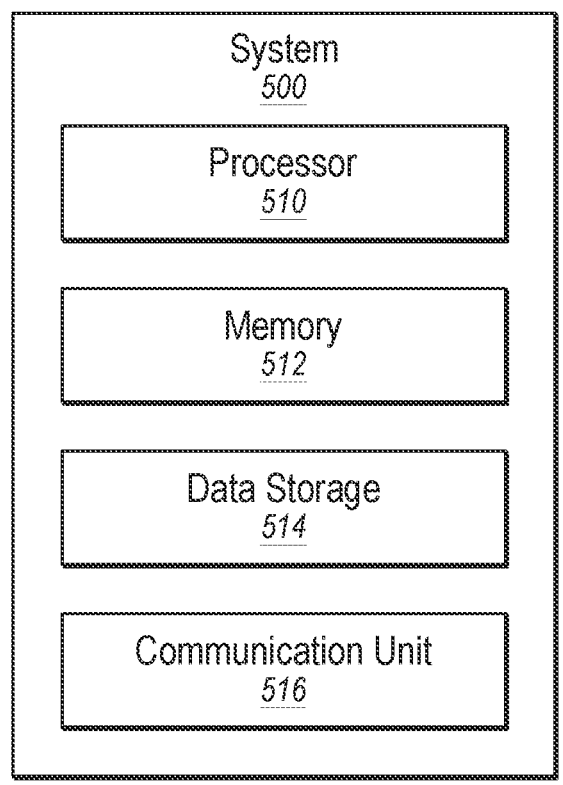
FIG. 5 illustrates a block diagram of an example computing system; all according to at least one embodiment described in the present disclosure.

FIG. 5 illustrates a block diagram of an example computing system 500, according to at least one embodiment of the present disclosure. The computing system 500 may be configured to implement or direct one or more operations associated with computing device (e.g., the computing device 102, the client computing device 124, the remote computing device 126, the additional computing device 127, or some combination thereof of FIG. 1). The computing system 500 may include a processor 510, a memory 512, a data storage 514, and a communication unit 516. The processor 510, the memory 512, the data storage 514, and the communication unit 516 may be communicatively coupled.

In general, the processor 510 may include any suitable special-purpose or general-purpose computer, computing entity, or processing device including various computer hardware or software modules and may be configured to execute instructions stored on any applicable computer-readable storage media. For example, the processor 510 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 5, the processor 510 may include any number of processors configured to, individually or collectively, perform or direct performance of any number of operations described in the present disclosure. Additionally, one or more of the processors may be present on one or more different electronic devices, such as different servers.

In some embodiments, the processor 510 may be configured to interpret and/or execute program instructions and/or process data stored in the memory 512, the data storage 514, or the memory 512 and the data storage 514. In some embodiments, the processor 510 may fetch program instructions from the data storage 514 and load the program instructions in the memory 512. After the program instructions are loaded into the memory 512, the processor 510 may execute the program instructions.

The processor 510 may fetch the program instructions from the data storage 514 and may load the program instructions in the memory 512. After the program instructions are loaded into memory 512, the processor 510 may execute the program instructions such that the computing system 500 may implement the operations as directed by the instructions.

The memory 512 and the data storage 514 may include computer-readable storage media for carrying or having computer-executable instructions or data structures stored thereon. Such computer-readable storage media may include any available media that may be accessed by a general-purpose or special-purpose computer, such as the processor 510. By way of example, and not limitation, such computer-readable storage media may include tangible or non-transitory computer-readable storage media including RAM, ROM, EEPROM, CD-ROM, or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 510 to perform a certain operation or group of operations.

The communication unit 516 may include any component, device, system, or combination thereof that is configured to transmit or receive information over a network. In some embodiments, the communication unit 516 may communicate with other devices at other locations, the same location, or even other components within the same system. For example, the communication unit 516 may include a modem, a network card (wireless or wired), an infrared communication device, a wireless communication device (such as an antenna), and/or chipset (such as a Bluetooth® device, an 802.6 device (e.g., Metropolitan Area Network (MAN)), a WiFi device, a WiMax device, cellular communication facilities, etc.), and/or the like. The communication unit 516 may permit data to be exchanged with a network and/or any other devices or systems described in the present disclosure.

Modifications, additions, or omissions may be made to the computing system 500 without departing from the scope of the present disclosure. For example, in some embodiments, the computing system 500 may include any number of other components that may not be explicitly illustrated or described.

Embodiments described in the present disclosure may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions may include, for example, instructions and data, which cause a general-purpose computer, special purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are described as example forms of implementing the claims.

As used in the present disclosure, terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in the present disclosure are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, various changes, substitutions, and alterations could be made hereto without departing from the spirit and scope of the present disclosure.

What is claimed is:

1. A computing device comprising:
   one or more computer-readable storage media configured to store instructions; and
   one or more processors communicatively coupled to the one or more computer-readable storage media and configured to, in response to execution of the instructions, cause the computing device to perform operations, the operations comprising:
   receiving, via a graphical user interface (GUI), a first user input effective to indicate a client visit between a client and a user is to start;
   instructing, based on the first user input, a video camera to capture a visit video of the client visit;
   receiving, via the GUI, a second user input effective to indicate a visit summary by the user is to start;
   receiving the visit video from the video camera;

instructing, based on the second user input, the video camera to capture a summary video of the visit summary;

receiving the summary video from the video camera;

automatically saving the visit video and the summary video to a data storage location associated with the client; and authorizing a remote computing device to access the summary video saved to the data storage location to extract information from the summary video corresponding to the visit summary to a client record within a record application corresponding to the user.

2. The computing device of claim 1, wherein:

the data storage location comprises a transcription portion;

the automatically saving the visit video and the summary video to the data storage location comprises saving the summary video to the transcription portion; and the authorizing the remote computing device to access the summary video saved to the data storage location comprises authorizing the remote computing device to access only the summary video saved to the transcription portion.

3. The computing device of claim 1, wherein:

the data storage location comprises a cloud data storage location;

the operations further comprise automatically saving the visit video and the summary video to a local data storage location associated with the client in a local memory; and the authorizing the remote computing device to access the summary video comprises authorizing the remote computing device to access only the summary video saved to the cloud data storage location.

4. The computing device of claim 3, wherein the operations further comprise:

archiving the visit video and the summary video to an archival storage device; and deleting, based on the archiving, the visit video and the summary video saved to the cloud data storage location and the local data storage location based on the archiving.

5. The computing device of claim 1, wherein:

the data storage location comprises a cloud data storage location and a transcription portion;

the automatically saving the visit video and the summary video to the cloud data storage location comprises saving the summary video to the transcription portion and to a different portion of the cloud data storage location; and the authorizing the remote computing device to access the summary video saved to the cloud data storage location comprises authorizing the remote computing device to access only the summary video saved to the transcription portion.

6. The computing device of claim 5, wherein the authorizing the remote computing device to access the summary video comprises authorizing the remote computing device to delete the summary video saved to the transcription portion.

7. The computing device of claim 1, wherein the second user input is also effective to indicate that the client visit with the user has ended.

8. The computing device of claim 1, wherein the operations further comprise:

receiving a third user input effective to identify the client; and naming the data storage location based on the identity of the client.

9. The computing device of claim 1, wherein:

the visit video comprises video data representative of audio captured by a microphone during the client visit and visuals within a scene captured by the video camera during the client visit; and the summary video comprises video data representative of audio captured by the microphone during the visit summary and visuals within a scene captured by the video camera during the visit summary.

10. The computing device of claim 1, wherein:

the data storage location comprises a cloud data storage location;

the operations further comprise:

generating a resource locator link corresponding to at least one of the visit video or the summary video saved to the cloud data storage location; and providing the resource locator link to a client computing device of the client.

11. The computing device of claim 1, wherein the user comprises a doctor, the client comprises a patient, and the record application comprises an electronic medical record.

12. The computing device of claim 1, wherein the remote computing device is configured to manually extract the information from the summary video to the client record within the record application corresponding to the user or to extract the information from the summary video to the client record within the record application using an artificial intelligence program.

13. A method comprising:

receiving, via a graphical user interface (GUI), a first user input effective to indicate a client visit between a client and a user is to start;

instructing, based on the first user input, a video camera to capture a visit video of the client visit;

receiving, via the GUI, a second user input effective to indicate a visit summary by the user is to start;

receiving the visit video from the video camera;

instructing, based on the second user input, the video camera to capture a summary video of the visit summary;

receiving the summary video from the video camera;

automatically saving the visit video and the summary video to a data storage location associated with the client; and authorizing a remote computing device to access the summary video saved to the data storage location to extract information from the summary video corresponding to the visit summary to a client record within a record application corresponding to the user.

14. The method of claim 13, wherein:

the automatically saving the visit video and the summary video to the data storage location comprises saving the summary video to a transcription portion of the data storage location; and the authorizing the remote computing device to access the summary video saved to the data storage location comprises authorizing the remote computing device to access only the summary video saved to the transcription portion.

15. The method of claim 13, wherein:

the data storage location comprises a cloud data storage location;

the method further comprises automatically saving the visit video and the summary video to a local data storage location associated with the client in a local memory; and the authorizing the remote computing device to access the summary video comprises authorizing the remote computing device to access only the summary video saved to the cloud data storage location.

16. The method of claim 15 further comprising:

archiving the visit video and the summary video to an archival storage device; and deleting, based on the archiving, the visit video and the summary video saved to the cloud data storage location and the local data storage location based on the archiving.

17. The method of claim 13, wherein:

the data storage location comprises a cloud data storage location and a transcription portion;

the automatically saving the visit video and the summary video to the cloud data storage location comprises saving the summary video to the transcription portion and to a different portion of the cloud data storage location; and the authorizing the remote computing device to access the summary video saved to the cloud data storage location comprises authorizing the remote computing device to access only the summary video saved to the transcription portion.

18. The method of claim 17, wherein the authorizing the remote computing device to access the summary video comprises authorizing the remote computing device to delete the summary video saved to the transcription portion.

19. The method of claim 13 further comprising:

receiving a third user input effective to identify the client; and naming the data storage location based on the identity of the client.

20. The method of claim 13, wherein:

the data storage location comprises a cloud data storage location; and the method further comprises:

generating a resource locator link corresponding to at least one of the visit video or the summary video saved to the cloud data storage location; and providing the resource locator link to a client computing device of the client.

* * * * *